United States Patent
Prichard et al.

(10) Patent No.: US 11,959,060 B1
(45) Date of Patent: Apr. 16, 2024

(54) FLUID SYSTEMS, APPARATUSES, DEVICES AND METHODS OF MANAGEMENT THEREOF FOR CULTIVATING TISSUE

(71) Applicant: Humacyte, Inc., Durham, NC (US)

(72) Inventors: Heather L. Prichard, Wake Forest, NC (US); Dustin Cashman, Chapel Hill, NC (US); Joshua McCall, Seattle, WA (US); Laura E. Niklason, Greenwich, CT (US); Benjamin Orbon, Cary, NC (US); Justin T. Strader, Durham, NC (US)

(73) Assignee: HUMACYTE, INC., Durham, NC (US)

( * ) Notice: Subject to any disclaimer, the term of this patent is extended or adjusted under 35 U.S.C. 154(b) by 611 days.

(21) Appl. No.: 16/875,897

(22) Filed: May 15, 2020

Related U.S. Application Data (60) Provisional application No. 62/849,478, filed on May 17, 2019.

(51) Int. Cl.
  *C12M 1/00* (2006.01)
  *C12M 1/34* (2006.01)

(52) U.S. Cl.
  CPC ............ *C12M 29/14* (2013.01); *C12M 23/14* (2013.01); *C12M 29/26* (2013.01); *C12M 41/12* (2013.01); *C12M 41/40* (2013.01)

(58) Field of Classification Search
  CPC ...... C12M 29/14; C12M 23/14; C12M 29/26; C12M 41/12; C12M 41/40
  See application file for complete search history.

(56) References Cited

U.S. PATENT DOCUMENTS

| 3,388,574 A | 6/1968 | Vincent |
| 3,606,596 A | 9/1971 | Edwards |

(Continued)

FOREIGN PATENT DOCUMENTS

| CN | 108440045 A | 8/2018 |
| DE | 102016208552 B3 | 4/2017 |

(Continued)

OTHER PUBLICATIONS

CableTiesAndMore. "Braided Cable Sleeving", Dec. 24, 2017, 2 pages. Retrieved Dec. 11, 2021 from WebArchive. https://web.archive.org/web/20171224205238/https://www.cabletiesandmore.com/BraidedSleeving.php.

(Continued)

*Primary Examiner* — William H. Beisner
*Assistant Examiner* — Danielle B Henkel
(74) *Attorney, Agent, or Firm* — COOLEY LLP (57) ABSTRACT

Embodiments of the present disclosure are directed to systems, apparatuses, devices and methods for tissue cultivating. Such systems may comprise a plurality of bioreactors, each bioreactor comprising a bag having a mandrel tube arranged therein, and a fluid management system for managing fluid flow among the plurality of bioreactors. The fluid management system can include at least one intra-luminal pump, configured to flow intra-luminal fluid in a first direction in the bioreactors, at least one media pump, configured to flow biomedia fluid in the bioreactors in a second direction opposite to the first direction, and a plurality of valves and/or clamps to effect at least one of filling, flowing, cessation of flow, and draining of at least one of the intra-luminal fluid and biomedia fluid tubes among the bioreactors.

28 Claims, 9 Drawing Sheets

(56) References Cited

U.S. PATENT DOCUMENTS

| | | | |
|---|---|---|---|
| 4,519,754 A | 5/1985 | Minick | |
| 4,925,376 A | 5/1990 | Kahler | |
| 5,447,417 A | 9/1995 | Kuhl et al. | |
| 5,470,744 A | 11/1995 | Astle | |
| 5,547,329 A | 8/1996 | Hirai et al. | |
| 6,129,428 A | 10/2000 | Helwig et al. | |
| 6,475,776 B1 | 11/2002 | Higuchi | |
| 7,878,786 B2 | 2/2011 | Yost et al. | |
| 10,085,829 B2 | 10/2018 | Soletti et al. | |
| 2004/0219659 A1* | 11/2004 | Altman | C12M 29/10 435/284.1 |
| 2004/0241835 A1 | 12/2004 | Hutmacher et al. | |
| 2005/0009178 A1 | 1/2005 | Yost et al. | |
| 2005/0069401 A1 | 3/2005 | Malin | |
| 2005/0084955 A1 | 4/2005 | Tamaoki et al. | |
| 2008/0032278 A1 | 2/2008 | Jones | |
| 2008/0220506 A1 | 9/2008 | Yost et al. | |
| 2008/0234806 A1* | 9/2008 | Dancu | G09B 23/28 435/375 |
| 2009/0042293 A1 | 2/2009 | Hata et al. | |
| 2010/0105138 A1* | 4/2010 | Dodd | C12M 29/00 435/289.1 |
| 2011/0207209 A1 | 8/2011 | Hammons et al. | |
| 2011/0319823 A1 | 12/2011 | Bojan et al. | |
| 2012/0028234 A1 | 2/2012 | Guertin et al. | |
| 2012/0251275 A1 | 10/2012 | Malin | |
| 2013/0109007 A1 | 5/2013 | Akra et al. | |
| 2013/0119284 A1 | 5/2013 | Fukano et al. | |
| 2018/0016540 A1 | 1/2018 | Sekine et al. | |
| 2018/0058437 A1 | 3/2018 | Eilers et al. | |
| 2018/0371394 A1 | 12/2018 | Ho et al. | |
| 2020/0392449 A1* | 12/2020 | Griffin | C12M 23/58 |
| 2021/0207073 A1 | 7/2021 | Tanabe et al. | |

FOREIGN PATENT DOCUMENTS

| | | | |
|---|---|---|---|
| JP | 2006149232 A | 6/2006 | |
| JP | 2018139615 A | 9/2018 | |
| WO | WO-2012170878 A2 * | 12/2012 | C12M 21/08 |

OTHER PUBLICATIONS

Discussion of servomotors and braking systems; ResearchGate. 2013, 9 pages. Retrieved Dec. 11, 2021. Servomotors with stable position when unpowered? | ResearchGate.

* cited by examiner

FLUID SYSTEMS, APPARATUSES, DEVICES AND METHODS OF MANAGEMENT THEREOF FOR CULTIVATING TISSUE

RELATED APPLICATIONS

This disclosure claims benefit of and priority to U.S. provisional patent application No. 62/849,478, filed May 17, 2019. The entire disclosure, in its entirety, is herein incorporated by reference.

BACKGROUND

There is a considerable need for tissue, e.g., vascular grafts, when the patient's own tissue is unavailable (e.g., damaged, diseased). When autologous tissue is not available, often times synthetic material is used (e.g., synthetic polytetrafluoroethylene (PTFE) for blood vessels). Other types of grafts, such as decellularized bovine tissue, and human allograft tissue, for example, from cadavers, can be used, but are prone to problems (e.g., in the case of blood vessels, aneurysm, calcification, and thrombosis). Thus, there is a need in the art for devices, systems, and methods configured to produce cost-effective tissue engineered constructs that can function long term, with minimal to no side effects, in vivo.

SUMMARY OF SOME OF THE EMBODIMENTS OF THE DISCLOSURE

Exemplary embodiments of the present disclosure are directed to systems, apparatuses, devices and methods of management thereof for at least one of cultivating and mass producing tissue for use in humans/mammals.

Accordingly, in some embodiments, a tissue cultivating system is provided and comprises a plurality of bioreactors, and a fluid management system configured to deliver one or more fluids to each bioreactor for cultivating tissue.

Such embodiments may include one and/or another (e.g., in some embodiments, a plurality of, and in further embodiments, all of) of the following additional features, structure, step, functionality, and/or clarifications, yielding yet further embodiments of the present disclosure:
 the bioreactors are arranged within at least one drawer or housing, which may comprise a plurality of drawers;
 an environmental control system configured to maintain the bioreactors at a predetermined temperature, humidity, and/or pressure;
 one or more organized fluid communication tubes configured to deliver one or more fluids at least to each drawer and/or each bioreactor to cultivate tissue;
 a controller for controlling at least one of operation of the system and one or more fluid flows of the fluid management system;
 the fluid management system can include a biomedia fluid reservoir configured to contain biomedia fluid having one or more nutrients and/or gases dissolved therein;
 the fluid management system can include an intra-luminal fluid reservoir configured to contain intra-luminal fluid, where the intra-luminal fluid can be configured to flow within each bioreactor, and/or, within a mandrel tube within each bioreactor, to optionally supply at least one of support, nutrients, and dissolved gases to cultivate tissue;
 one or more gas dissolving means for dissolving one or more gases in at least one of the biomedia fluid or corresponding reservoir, and intra-luminal fluid or corresponding reservoir, such means may comprise at least one of a sparger, and an inline gas media exchanger, or gas overlay in contact with biomedia fluid (e.g., for oxygenating the respective fluid received therein);
 means to adjust heights between the reservoirs and/or one or more of the drawers containing bioreactors;
 establishing a pressure differential between the intra-luminal fluid and biomedia fluid configured so as to provide, for example, a predetermined range of strain to each mandrel tube of each bioreactor (for example);
 each bioreactor can comprise a bag including one or more of: a first end and a second end, at least one biomedia fluid inlet; at least one biomedia fluid outlet; a/the mandrel tube arranged within the bioreactor, an intra-luminal fluid inlet connected to a first end of the mandrel tube, an intra-luminal fluid outlet connected to a second end of the mandrel tube, and a cell injection port;
 the fluid-management system can further comprise one or more fluid communication tubes comprising a biomedia fluid tube configured to direct biomedia fluid into and out of each bioreactor and/or an intra-luminal fluid tube configured to direct intra-luminal fluid through each mandrel tube;
 at least one tube organizer configured to at least one of arrange and direct a plurality of tubes among the bioreactors;
 at least one dampener arranged on at least one fluid supply line (or other fluid supply/return/waste line) to one or more of the bioreactors;
   the dampener can be configured to smooth out variability in pressure in at least one of the fluid flows to and/or from the bioreactors;
   the dampener can be arranged on an intra-luminal fluid inlet for supplying the bioreactors;
 at least one flow restrictor configured to restrict flow in at least one fluid flow to and/or from the bioreactors, where the at least one flow restrictor:
   can be arranged on an intra-luminal fluid outlet for the bioreactors,
   can be configured to control at least one of pressure and flowrate;
   can be configurable to provide different flow restriction functionality based on a change of at least one of internal diameter, length, and material thereof;
   can be arranged on a return line for returning intra-luminal fluid from one or more bioreactors to the intra-luminal fluid reservoir;
 at least one waste port configured to direct at least one of waste biomedia fluid and/or waste intra-luminal fluid out of the system, where the at least one waste port can include at least waste port valve associated therewith;
 the fluid management system can comprise or further comprise at least one of:
   at least one of: an intra-luminal fluid pump, a biomedia fluid pump (or a single pump with separate fluid-tight compartments to pump each fluid), and one or more (and preferably, a plurality of) valves and/or clamps arranged among a tube or the plurality of tubes;
   during a fill operation, at least one of the pumps, the valves, and the reservoirs can be configured to simultaneously fill each bioreactor with biomedia fluid from the biomedia fluid reservoir;
   during a fill operation, each mandrel tube of each bioreactor can be filled with intra-luminal fluid from the intra-luminal fluid reservoir;

a fill operation can be configured to remove substantially all pockets of gas or air that are not dissolved within the biomedia, from each bioreactor and/or associated mandrel tubes;

during a processing operation, the pumps, valves, and reservoirs can be configured to circulate biomedia fluid between the biomedia fluid reservoir serially or in parallel through the plurality of bioreactors one after another;

during a processing operation, intra-luminal fluid can be circulated serially or in parallel through each of the mandrel tubes of the bioreactors, one after another;

the flow of intra-luminal fluid through the bioreactors can be in direction opposite to the serial flow of biomedia fluid reservoir through the bioreactors, or, the flow of intra-luminal fluid through the bioreactors can be in a same direction as that of the serial flow of biomedia fluid reservoir through the bioreactors; and during a drain operation, the pumps, valves, and reservoirs are configured to simultaneously drain each bioreactor of biomedia fluid, either in series or in parallel;

a sequence of a drain and/or a fill processes for a bioreactor or a plurality of bioreactors can be completed in a duration that is suitable for cell culture.

Accordingly, in some embodiments, a tissue cultivating method is provided which includes optionally providing the system according to any of the disclosed embodiments, optionally seeding each of the plurality of bioreactors with cells, and flowing one or more fluids through each bioreactor configured to aid in cultivating tissue.

Such embodiments may include one and/or another (i.e., a plurality of, and in some embodiments, all of) of the following additional features, structure, step, functionality, and/or clarifications, which corresponds to yet further embodiments of the present disclosure:

the one or more fluids can comprise a biomedia fluid having one or more nutrients and/or gases dissolved therein;

the one or more fluids can comprise intra-luminal fluid;

dissolving one or more gases in at least one of the biomedia fluid and intra-luminal fluid;

adjusting heights between two or more reservoirs and/or one or more components of the system;

configuring the system so as to conduct a filling operation;

during a fill operation, each bioreactor can be filled with the one or more fluids simultaneously in parallel or in series;

the fill operation results in the removal of substantially all undissolved pockets of gasses from each bioreactor;

configuring the system to operate in a processing operation;

during a processing operation, the one or more fluids are circulated between the bioreactors serially or in parallel;

the system can be configured to operate in a drain operation; and circulation of intra-luminal fluid serially through each of the bioreactors, one after another, can be established in a direction opposite to the serial or parallel flow of biomedia fluid through the bioreactors, or in a same direction.

Accordingly, in some embodiments, a tissue cultivating system is provided which includes at least one: biomedia fluid reservoir configured to contain biomedia fluid having one or more nutrients and a dissolved gas therein, an intra-luminal fluid reservoir configured to contain intra-luminal fluid having a gas dissolved therein, where at least one of the biomedia fluid reservoir and the intra-luminal fluid reservoir includes means for oxygenating the respective fluid received therein. In some embodiments, the system may also include a plurality of bioreactors (i.e., a plurality corresponding to "N" bioreactors, e.g., between 2-200, 2 and 100, 2-50 bioreactors), each bioreactor comprising a bag having:

a first end and a second end each with an end cap,
at least one biomedia fluid inlet,
at least one biomedia fluid outlet,
a mandrel tube arranged within the bag,
an intra-luminal fluid inlet connected to a first end of the mandrel tube,
an intra-luminal fluid outlet connected to a second end of the mandrel tube, and
a cell injection port;

Such embodiments may further include at least one of:

a plurality of fluid communications tubes comprising at least: a biomedia fluid tube configured to direct biomedia fluid into and/or out of each bioreactor; an intra-luminal fluid tube configured to direct intra-luminal fluid into and/or out of each mandrel tube, at least one tube organizer configured to at least one of arrange and direct a plurality of tubes having first ends or connections thereto located outside the arrangement of bioreactors, at least one flow resistor arranged on a return line for returning intra-luminal fluid from an intra-luminal media tube associated with a last mandrel tube of a last bioreactors to the intra-luminal fluid reservoir;

at least one waste port configured to direct at least one of waste biomedia fluid and waste intra-luminal fluid out of the system, the at least one waste port including at least waste port valve associated therewith;

and a fluid management system for managing fluid flow among at least one of the mandrel tubes, the intra-luminal fluid tube(s), the biomedia fluid reservoir, the intra-luminal fluid reservoir, and the bioreactors.

The fluid management system may include at least one of: an intra-luminal pump, a biomedia pump, and a plurality of valves and/or clamps arranged among the plurality of tubes.

The fluid management system may be configured such that:

during a during a fill operation, the pumps, valves, and reservoirs are configured to substantially simultaneously filling each bioreactor with biomedia fluid from the biomedia fluid reservoir and intra-luminal fluid from the intra-luminal fluid reservoir using respective biomedia fluid and intra-luminal fluid tubes, the fill operation resulting in the removal of substantially all undissolved gas pockets from each bioreactor and associated mandrel tubes and intra-luminal fluid tubes;

during a processing operation the pumps, valves, and reservoirs are configured to: circulate biomedia fluid between the biomedia fluid reservoir serially or in parallel through the plurality of bioreactors, and circulate intra-luminal fluid serially or in parallel through each of the mandrel tubes of the bioreactors, and during a drain or fill operation, the pumps, valves, and reservoirs are configured to substantially simultaneously drain or fill each bioreactor of biomedia fluid, and in some embodiments, within a predetermined period of time (e.g., between 2 min and 60 min, between 2 min and 30 min, between 5 min and 15 min, and the like);

In such embodiments:

an environmental control system may be included and configured to control at least one of the temperature and humidity within the incubator shell; and the circulation of intra-luminal fluid serially or in parallel through each of the mandrel tubes of the bioreactors, can be established in a direction opposite to the serial flow of biomedia fluid reservoir through the bioreactors, or in a same direction.

In some embodiments, a tissue cultivating system is provided which includes a plurality of bioreactors, each bioreactor comprising a bag having a mandrel tube arranged therein, and a fluid management system for managing fluid flow among the plurality of bioreactors. The fluid management system can include:

at least one intra-luminal pump, configured to flow intra-luminal fluid in a first direction in the bioreactors;

at least one media pump, configured to flow biomedia fluid in the bioreactors in a second direction opposite to the first direction; and a plurality of valves and/or clamps to effect at least one of filling, flowing, cessation of flow, and draining of at least one of the intra-luminal fluid and biomedia fluid tubes among the bioreactors.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The above-noted embodiments will become even more evident by reference to the following detailed description and accompanying drawings.

BRIEF DESCRIPTION OF THE DRAWINGS

The skilled artisan will understand that the drawings of this disclosure are primarily for illustrative purposes and are not intended to limit the scope of inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
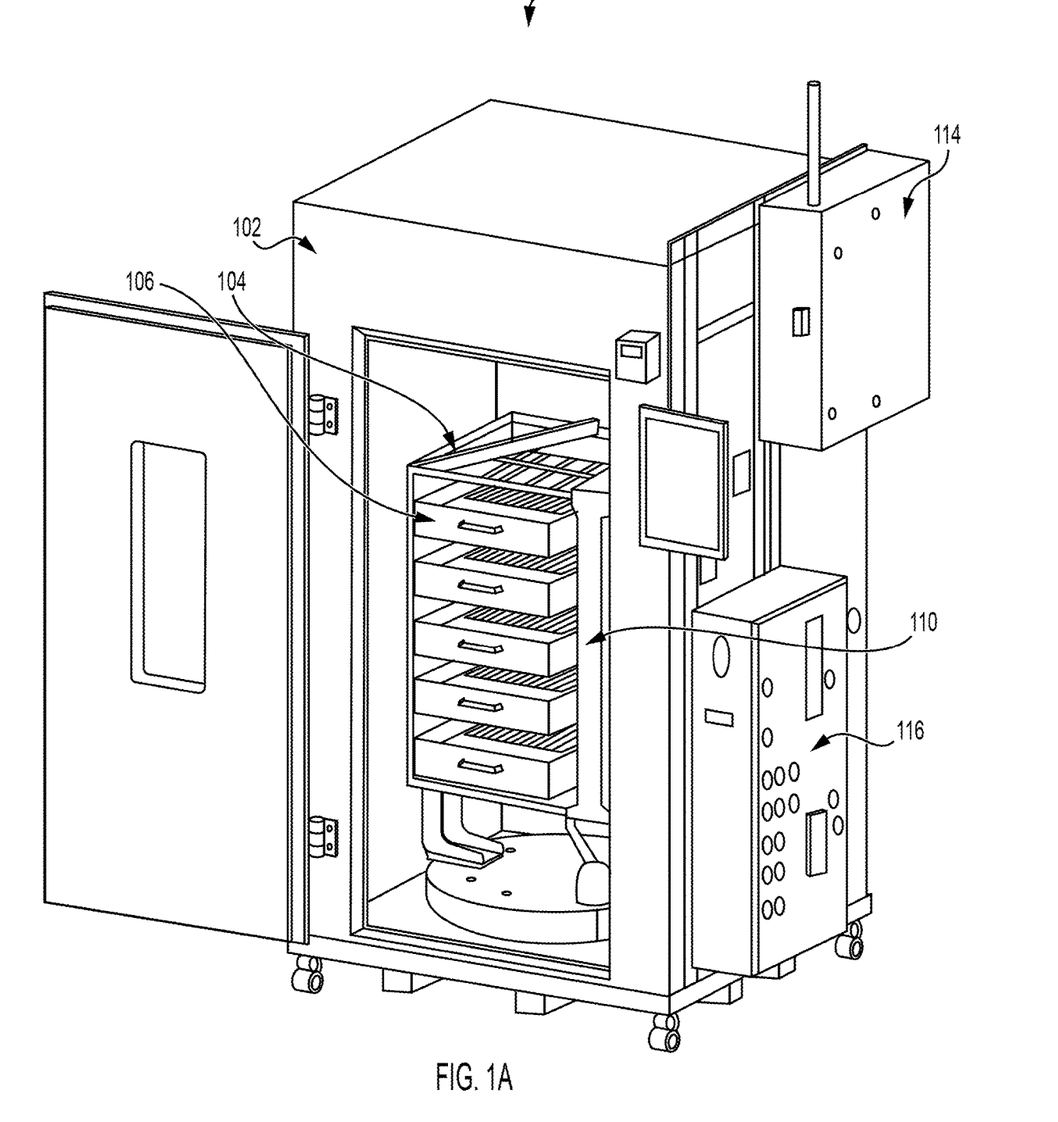
FIGS. 1A-C show example embodiment of a tissue cultivating system or an incubator used for producing human acellular vessels (HAVs) that can be used to replace diseased or damaged blood vessels in patients, according to some embodiments.
Figure 1B:
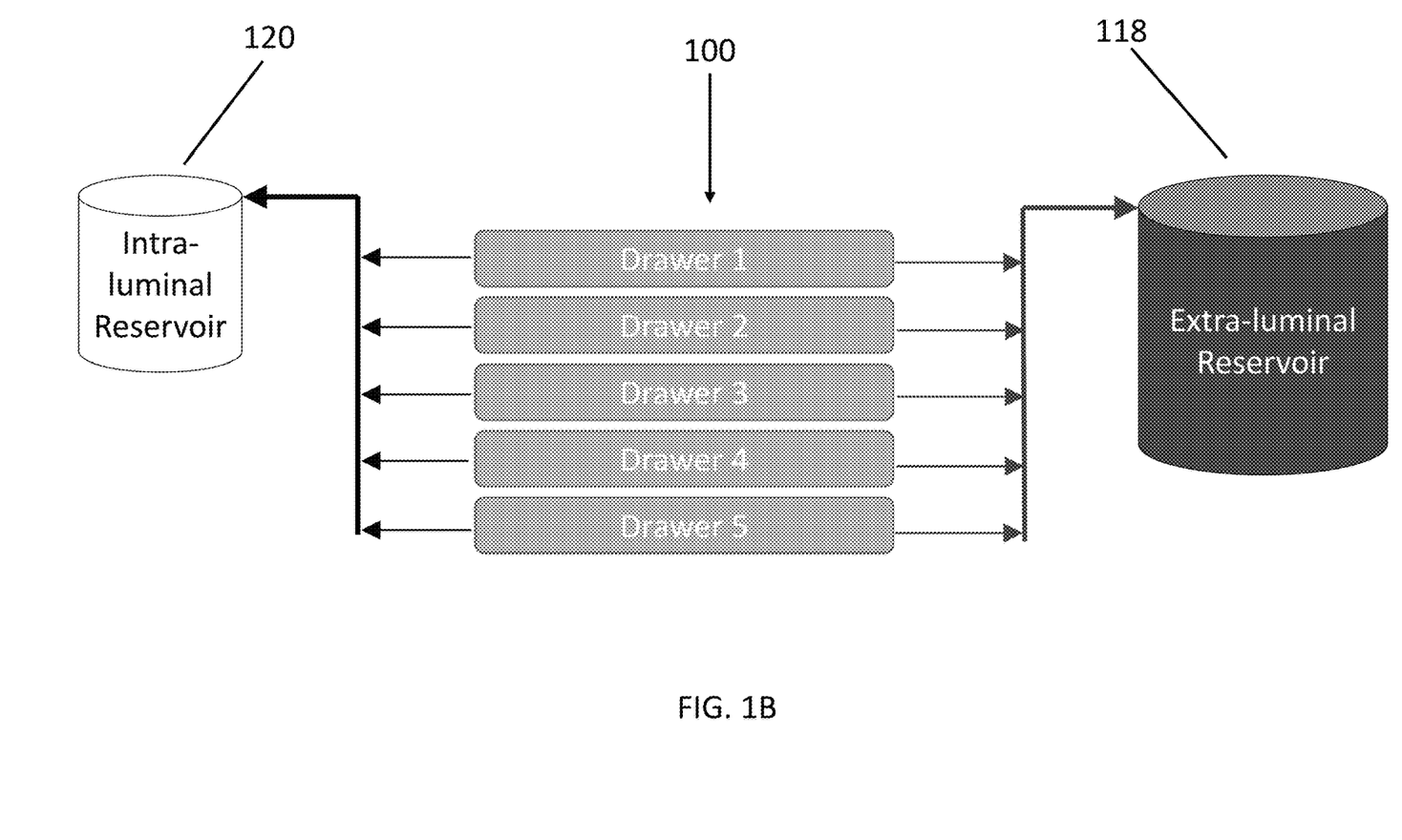
Figure 1C:
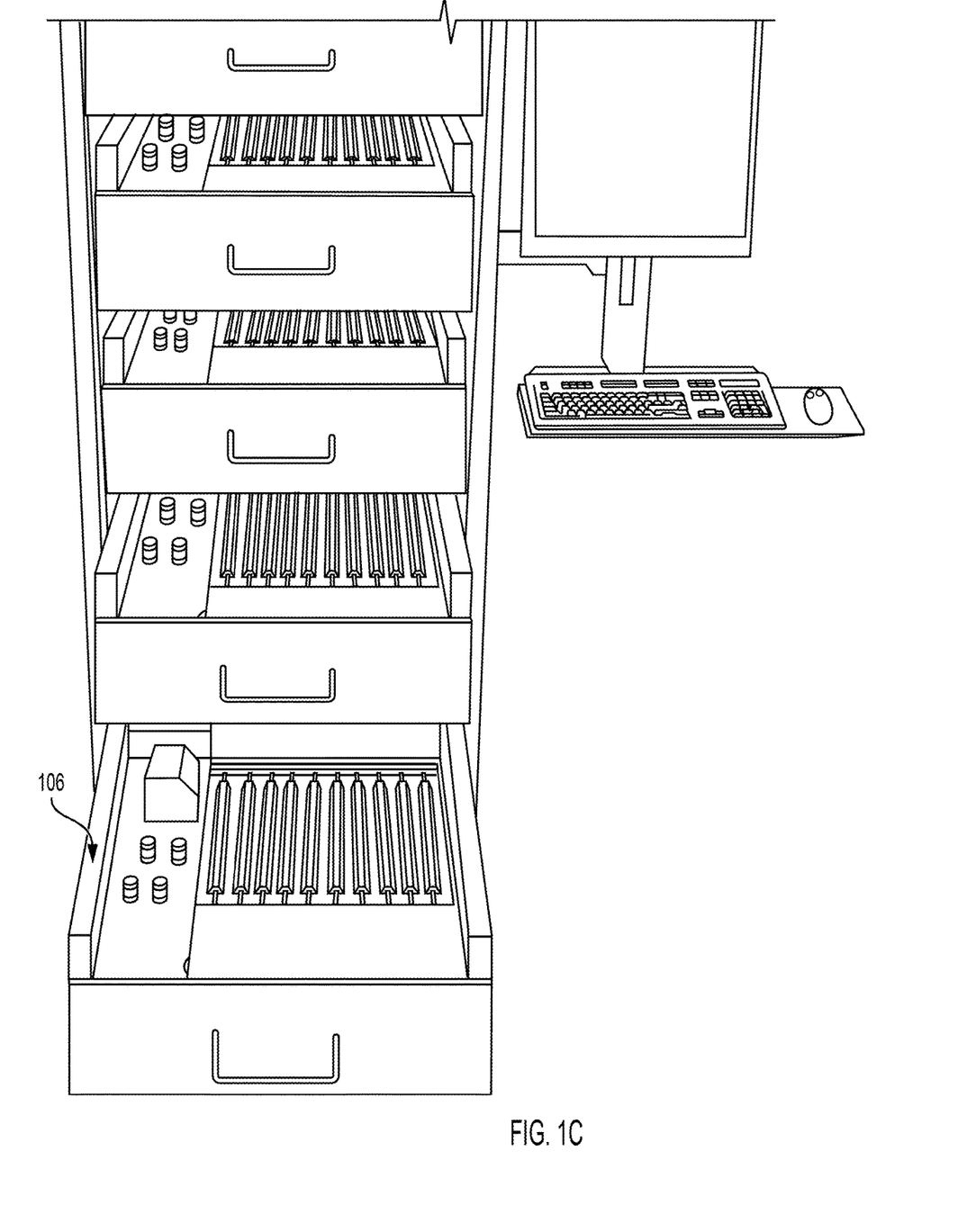

FIGS. 1A-C show example embodiments of a tissue cultivating system for incubating/producing tissue. In some embodiments, the system may be used to produce human acellular vessels (HAVs) that can be used to replace diseased or damaged blood vessels in patients. Specifically, and again for example, blood vessels damaged as a result of complications caused by various diseases or caused by trauma can be replaced by HAVs. The disclosed embodiments can also be used to produce other tissues of the body.

Accordingly, as shown in FIGS. 1A-C, in some embodiments, incubator 100 includes an incubator shell 102, having an access opening, which may include a door, a drawer cage 104 which may be positioned within the incubator shell 102 and may be configured for receiving one or more drawers 106 (which may be arranged on a frame/housing within the shell 102).

The flow of one or more fluids through the drawers 106 can be controlled by a cage/fluid management module (CFM) 110 that is coupled to the one or more drawers (or frame/housing holding the drawers), including being physically attached, and may include any of (in some embodiments, a plurality of, and in some embodiments, all of) one or more pumps (e.g., peristaltic pumps), one or more sensors (e.g., pressure sensors), one more tubes/pneumatic connections for facilitating the transfer of fluids within the drawers, electrical components and connections for powering the electronics onboard and/or communicating with controller modules (e.g., external or onboard the incubator), and/or the like. In some embodiments, the incubator 100 may also include an environmental control module or system that facilitates the management of the incubator's environmental characteristics, including but not limited to temperature, humidity, pressure, etc. For example, the system may include incubator connections that facilitate the heating, cooling, humidifying, dehumidifying, increasing pressure and/or decreasing pressure of the incubator.

In some embodiments, the incubator 100 may include a controller module 114 that can be configured to provide a user to interface with and control of the incubator. For example, the controller module 114 may be coupled to the incubator (e.g., including being physically attached to the incubator shell 102) and may include a human machine interface (HMI) that is configured to allow a user such as an incubator technician, an HAV production worker, etc., to interact with the incubator 100 (e.g., input instructions/data and/or receive data back from the incubator, with the instructions/data including but not limited to incubator status, internal parameters such as pressure, temperature, etc.). In some embodiments, the controller module 114 may also include a programmable logic controller (PLC) that is configured to facilitate the automation of the HAV production process by the incubator. In some embodiments, the controller module 114 may be configured to communicate wirelessly and/or in a wired setting to another device (e.g., server, computer, mobile device).

In some embodiments, the incubator 100 may also include a materials management module (MMM) 116. The MMM 116 may be coupled (e.g., including being physically attached) to the incubator shell 102, but it can be located anywhere proximate the incubator and may be fluidly connected thereto (as well as fluidly connected to the drawers and/or bioreactors). The MMM may be configured to manage the flow of media in the incubator, the drawer(s), and/or among one or more bioreactors arranged within each drawer, and in some embodiments, between the forgoing and media reservoirs 118 (e.g., intra-luminal fluid or IL fluid for supply to a mandrel and/or tissue construct), 120 (e.g., extra-luminal fluid of EL fluid to supply, generally, to a bioreactor). Media reservoirs can be configured with fluid media that may include one or more dissolved gases, elements, nutrients and the like (the fluid may be a liquid or an air/gas flow). In some embodiments, means for adjusting relative heights between the reservoirs can be adjusted to adjust, for example, relative pressures between reservoirs. Such means may comprise one or more shelves, which can be adjusted for vertical distance (such adjustment may be automated via motors, gearing, actuators, and the like).

Gasses may be dissolved in fluid flows using, for example, at least one of a sparger, and membrane gas exchange apparatuses/systems, or gas overlay systems, that are familiar to those of skill in the art.

Figure 2A:
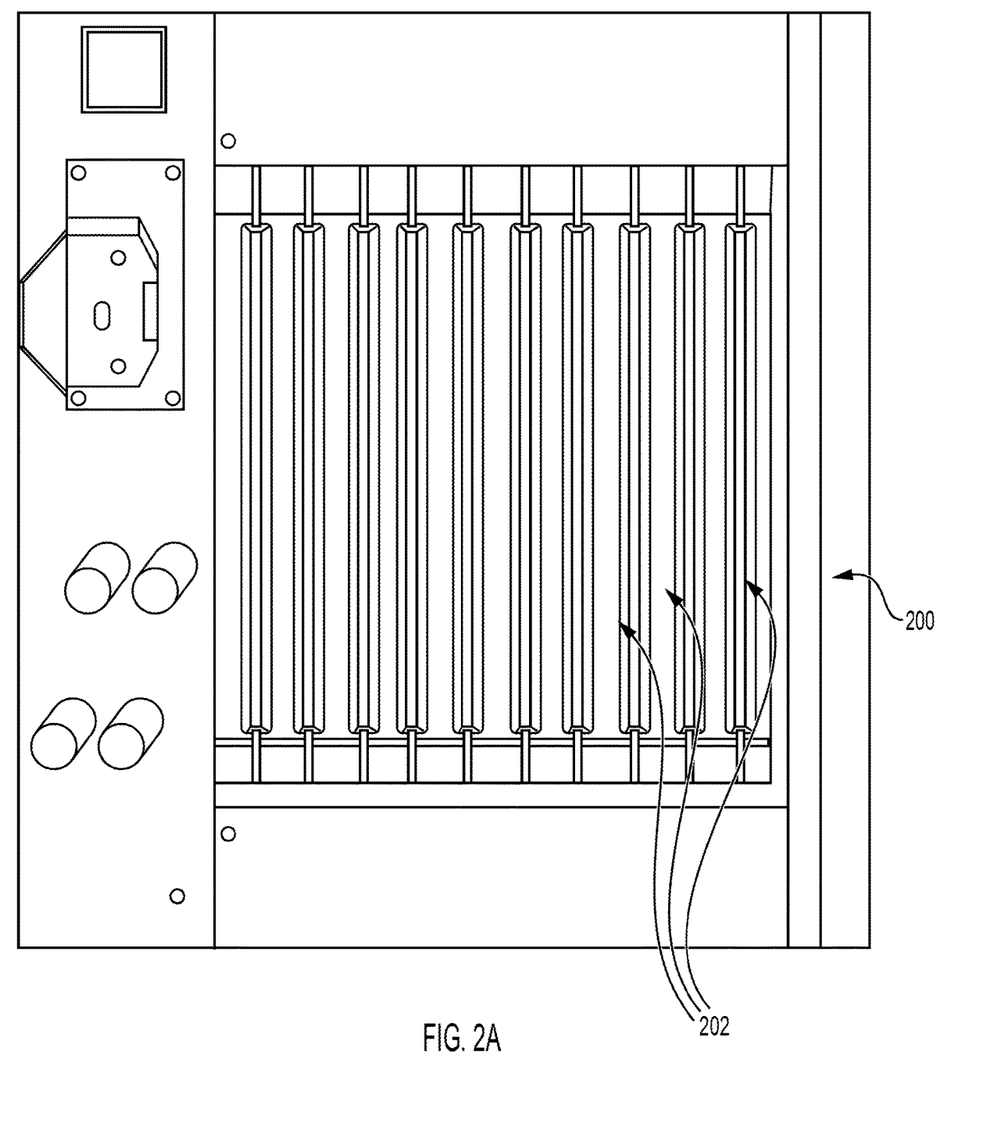
FIG. 2A shows a top view of an embodiment of an incubator drawer containing individual bioreactors, according to some embodiments of the disclosure.

FIG. 2A shows an example embodiment of a drawer for inclusion with the drawer cage. As shown, drawer 200, according to some embodiments, can include one or more (and preferably a plurality) of bioreactor systems ("bioreactors") 202 and components associated therewith.

Figure 2B:
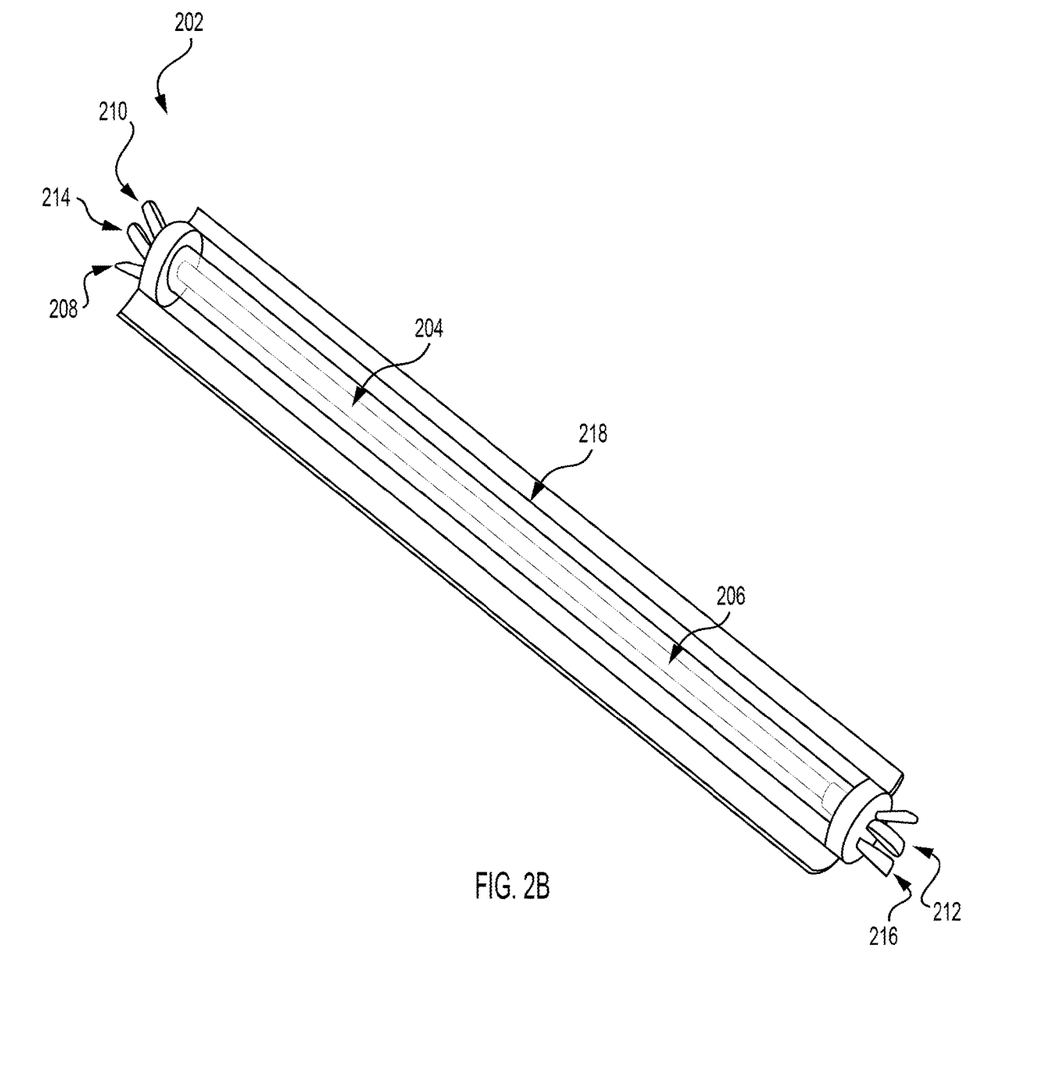
FIG. 2B shows a perspective view of an embodiment of a bioreactor, according to some embodiments of the disclosure.
Figure 2C:
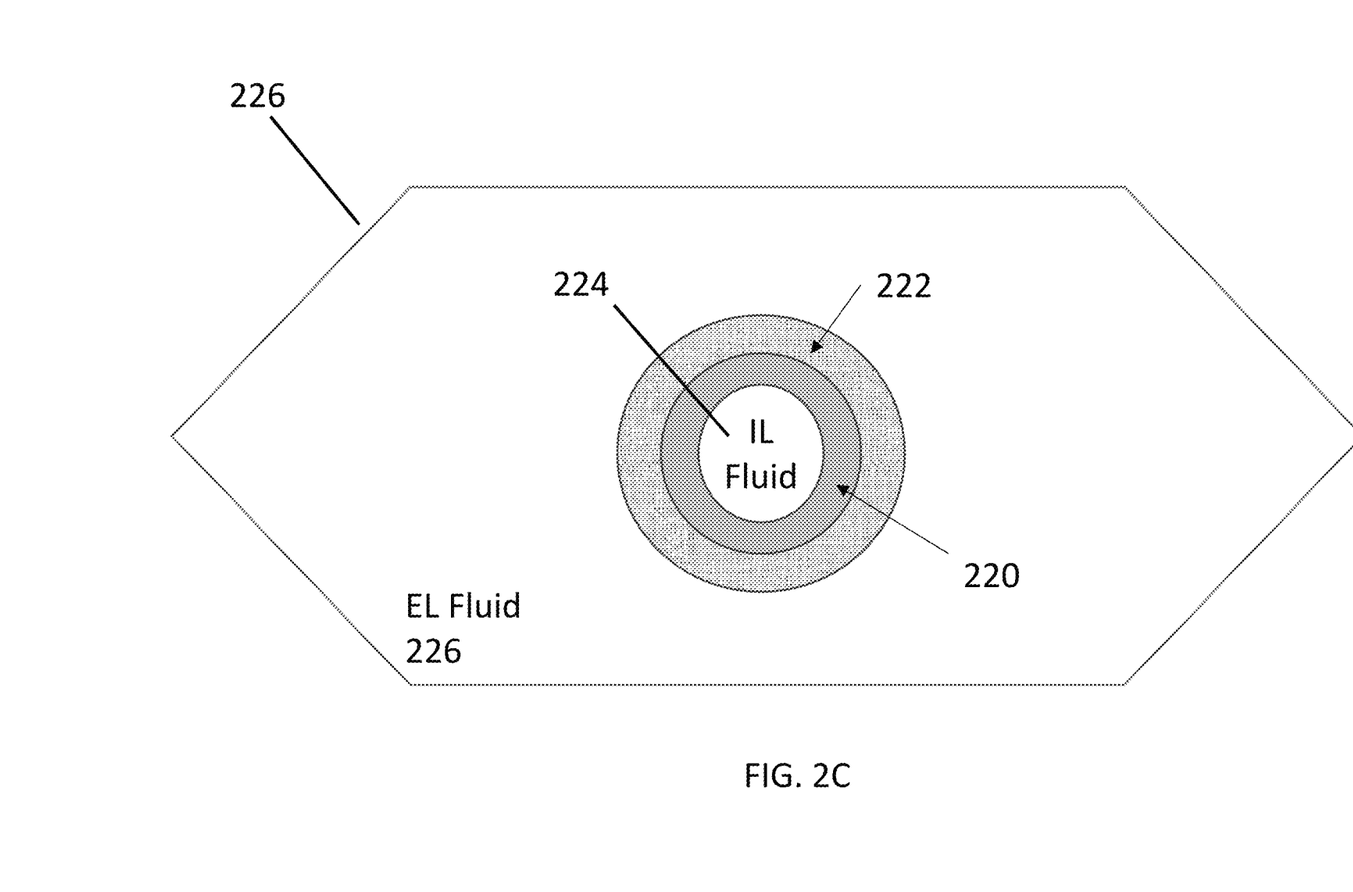
FIG. 2C shows a cross-sectional view of an embodiment of a bioreactor, according to some embodiments of the disclosure.

FIGS. 2B-C show a side and cross-sectional views of a bioreactor system ("bioreactor"), according to some embodiments, in which HAVs are produced. In some embodiments, the bioreactor 202 is configured to grow and process tissue, e.g., HAVs 206. Each bioreactor, with reference to producing an HAV, includes a mandrel tube 204, 220, which can comprise silicone (in some embodiments), which are used to support tissue scaffolds, e.g., tubular scaffolds made of polyglycolic acid (PGA) mesh, a biodegradable suture material onto which cells (e.g., human smooth muscle cells) can be placed in the process of creating an HAV 206.

The mandrel tube 204 may extend between the two ends of the bioreactor, the two ends of the mandrel each having a cuff that is attached to an end cap (e.g., ultra-low density polyethylene cap) of the bioreactor. In some embodiments, each bioreactor includes a housing or bag 218 made from ultra-low density polyethylene.

The bioreactor 202 may include a cell injection port 208 configured to receive biological cells for deposition on the scaffolds. Further, each bioreactor 202 may be configured to include one or more inlets 210 and/or outlets 212 for receiving and/or discharging, respectively, various biomedia, fluids and/or gases for treating (growing and/or removing) the deposited cells. For example, a biomedia inlet 210 can be included and configured for receiving a biomedia fluid and a biomedia outlet 212 for expelling the biomedia fluid after the fluid traverses through the bioreactor, washing over, for example, the scaffold contained within. In some embodiments, the biomedia fluid may include one or more nutrients and/or gases dissolved therein, for use in culturing the deposited cells.

In some embodiments, each bioreactor 202 may also include intra-luminal fluid inlet 214 and outlet 216 for receiving and expelling, respectively, intra-luminal fluids containing one or more dissolved gases, and/or nutrients, etc. For example, an intra-luminal fluid tube running between the intra-luminal fluid inlet 214 and the intra-luminal fluid outlet 216 may direct the intra-luminal fluids to traverse through the mandrel tube 204.

In some embodiments, the cells (e.g., the human smooth muscle cells) placed on the scaffold grow in vitro to form a biologic three dimensional (3D) scaffold matrix, which includes HAV tissues 206 generated as collagen matrix from the cells on the scaffold during the bioreactor system culturing process. As noted above, the generation of HAV tissues 206 from the cells deposited in the scaffold may be aided by the presence of biomedia, fluids, gases, etc., which may occur under conditions of at least substantially constant pressure and flow for a period of time. After the generation of HAV tissues 206, the HAVs may be de-cellularized to remove the cells, to reduce the potential immunogenicity of the HAV for patients by removing the antigenic cellular components of the HAVs.

As shown in FIG. 2C, which illustrates a cross-sectional view of a bioreactor 226, including the HAV, which is grown on/via a PGA mesh 222 (for example) over a mandrel (e.g., silicone tubing 220). The intra-luminal fluid 224 is flowed through the mandrel (or tissue construct) to supply nutrients to the growing HAV and eliminate waste, and EL fluid (e.g., extra-luminal fluid 226) which is supplied outside of the mandrel/tissue construct (for example).

In some embodiments, the incubator disclosed herein includes a plurality of tubes for transporting biomedia, intraluminal fluid, gases and/or the like from reservoirs (for example) to at least one of the incubator shell, the drawer cage, one or more of the drawers, and one or more of the bioreactors. With respect to the bioreactors, such fluid/gas communication is supplied to inlets at ends of the bioreactors, which is then discharged the same from the bioreactors via the outlets at the other ends of the bioreactors. In some embodiments, access to a drawer containing bioreactors (such as the one depicted in FIG. 2A) can be accomplished without having to disconnect the tubes from the MMM, the reservoirs, or the drawer/incubator, and/or the like. For example, a drawer may include a tube guide or organizer that is configured to at least arrange and/or direct one or more fluid communication tubes to allow at least one end of the drawer to be pulled out from the drawer cage without disconnecting one or more, or all tubes. For example, such a tube guide or organizer may be in the form of a plurality of grooves on a specific structure arranged proximate a drawer, and/or integral for formed within a side of a drawer, thereby connecting at least one of the drawers and/or bioreactors with external devices/systems (e.g., the reservoirs).

The one or more fluids/gases being transported to and/or from at least one of the incubator shell, the one or more drawers and the one or more bioreactors arranged in a drawer, via one or more fluid communication tubes can also include various valves, clamps, and the like so as to selectively at least one of restrict, enable, start, and stop the flow of a liquid or gas flowing through such tube(s). Some embodiments of the present disclosure correspond to the placement of one and/or another of the valves among one and/or another of one or more of the fluid communication tubes.

Further yet, one or more pumps can be included (which may be part of the MMM), so as to provide pressure and/or flowrate to one or more of the fluids being supplied (ultimately) to the bioreactors, controllable, in some embodiments, via a controller/processor.

Figure 3A:
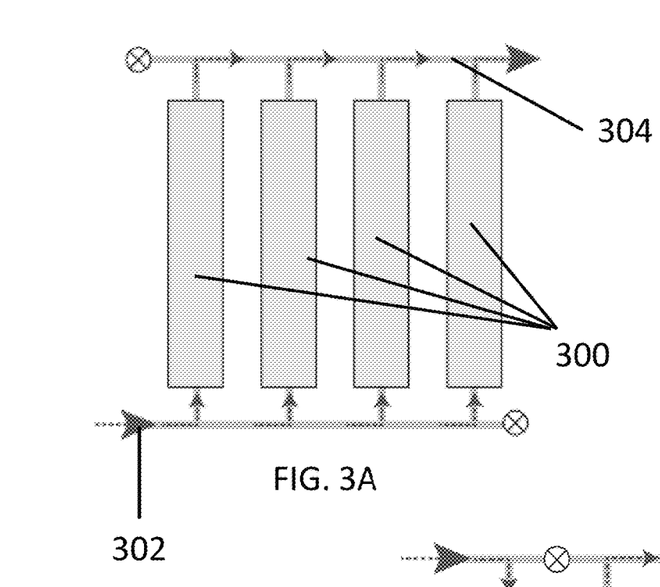
FIG. 3A-C represent various fluid flows (e.g., intra-luminal flows) through bioreactors according to some embodiments of the present disclosure.

As discussed above, a single drawer can include one or more bioreactors, and as such, there can be a plurality of ways for fluids to be supplied to, pass through, and exit, the bioreactors. For example, as shown in FIG. 3A, a fluid (e.g., biomedia fluid, intra-luminal fluid, or both) can flow through a plurality of bioreactors in a parallel manner, i.e., simultaneously; specifically, the arrows in the figure illustrate parallel flow of fluid through the plurality of bioreactors 300, via a common supply line 302, and a common return line 304 (for example and according to some embodiments). That is, and for example, a fluid from a source can be split (e.g., via various splitters, pumps, and/or valves arranged accordingly) so as to supply one and/or another inlet of each bioreactor (e.g., all). In such embodiments, such fluid/gas flow may be configured to flow through each bioreactor in a same direction before exiting through corresponding outlets thereof. In some embodiments, such parallel flow(s) are particularly useful for filling or draining all the bioreactors in a single operation (i.e., at a single time). For example, parallel flow operations can reduce or prevent cross contamination of bioreactors during a de-cellularization process (for example) where cells are removed after the formation of HAV tissues (for example). In some embodiments, the filling of all bioreactors in a parallel manner allows for efficient removal of non-dissolved gas pockets entrapped in the bioreactors (as the filling removes lower density fluids and gasses from the bioreactor systems). In some embodiments, if both biomedia fluid and intra-luminal fluid is supplied to each of the bioreactors, the direction at which each is provided may be in a same direction, or in some embodiments, may be supplied in opposite directions.

The valves which enable the parallel filling of the bioreactors can be valves which are manually and/or automatically operated for opening, closing, and limiting flow rates. For automatic operations, the valves can be controlled via a controller/processor, which can be programmable/operable for a particular task (e.g., filling, processing, emptying). In some embodiments, one or more sensors may be included, which may determine at least one of on, off, and flowrate of one or more valve(s), or one or more of the fluid communication tubes.

Figure 3B:
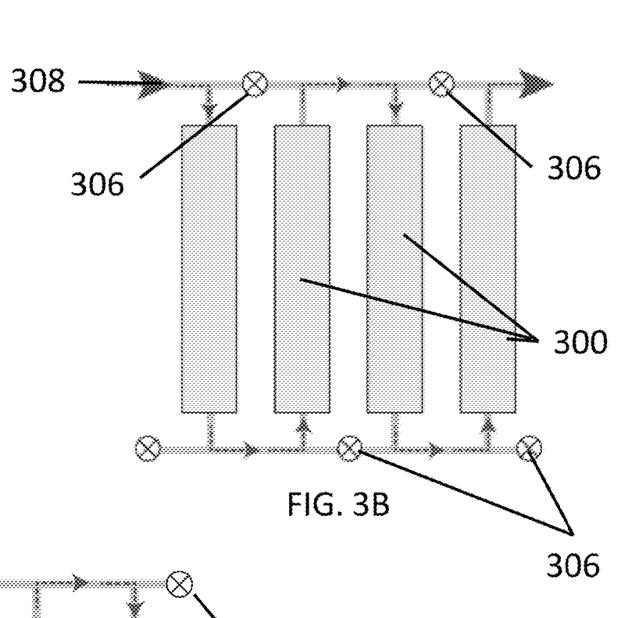

In some embodiments, FIG. 3B, a fluid (e.g., biomedia fluid, intra-luminal fluid, or both) may be flowed through a plurality of bioreactors in a serial manner. That is, the fluid may flow from a fluid source (e.g., reservoir) through an inlet into a first bioreactor before proceeding to a second bioreactor (and thereafter through N bioreactors) in a serial manner before exiting the last bioreactor via the respective bioreactor outlet. In some embodiments, such serial flows are particularly useful so as to expose tissue in each bioreactor to at least substantially the same fluid conditions as possible (e.g., flow rates, nutrient(s), metabolite(s), dissolved gas levels, etc.). The serial flow in the figure is evidenced by the arrows, such that, fluid flows from one bioreactor serially to another, and then other, with the fluid line 308 acts as both a feed and an ultimate return line. The foregoing is enabled, i.e., feeding a first bioreactor with fluid, and preventing the fluid from parallel entry into other bioreactors, via valves 306. Further, serial fluid flows, according to some embodiments, are beneficial for reducing and/or minimizing the use of pumps, valves, and/or fluid paths, etc., in producing tissue (e.g., HAVs), which in turn is helpful in avoiding or reducing the occurrence of cultivation failures. For example, the noted flows help reduce contamination in the tissue/HAV growth process.

Figure 3C:
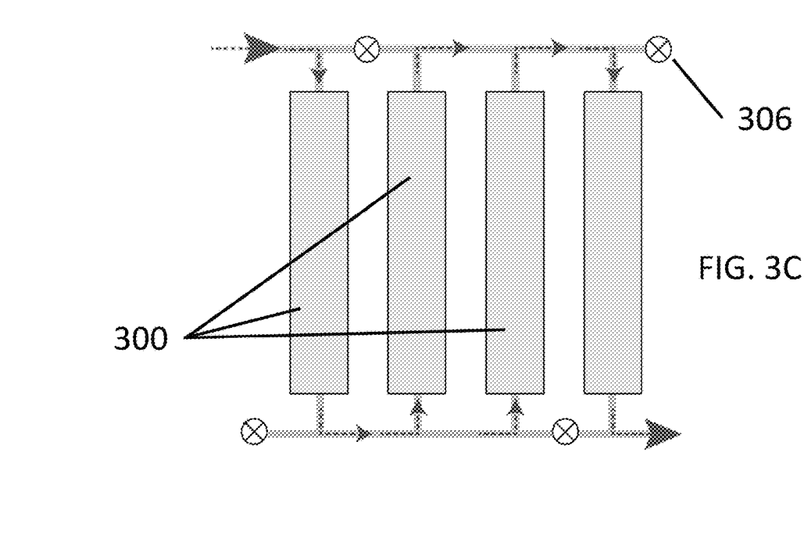

In some embodiments, a combination of parallel and serial fluid flows may be used when having a fluid pass through a plurality of bioreactors in a drawer, e.g., FIG. 3C, as evidenced by the arrows, and enabled by the switching of various valves 306. Such hybrid fluid flow can be used when one wishes to take advantage of the benefits of both serial and parallel fluid flow patterns, reducing contamination of bioreactors during de-cellularization (for example) while exposing the bioreactors 300 to at least substantially same fluid conditions as possible, for example. Supply and return lines are as illustrated (and again, dependent on valve positions). For example, fluids may pass through some of the bioreactors in a serial manner as described above, while flowing parallel through other set of bioreactors. Switching of valves to on/off positions can be either manual or via electronic/automated control (and incorporated in one or more controllers associated with the system according to various embodiments).

Figures 4A, 4B, 4C:
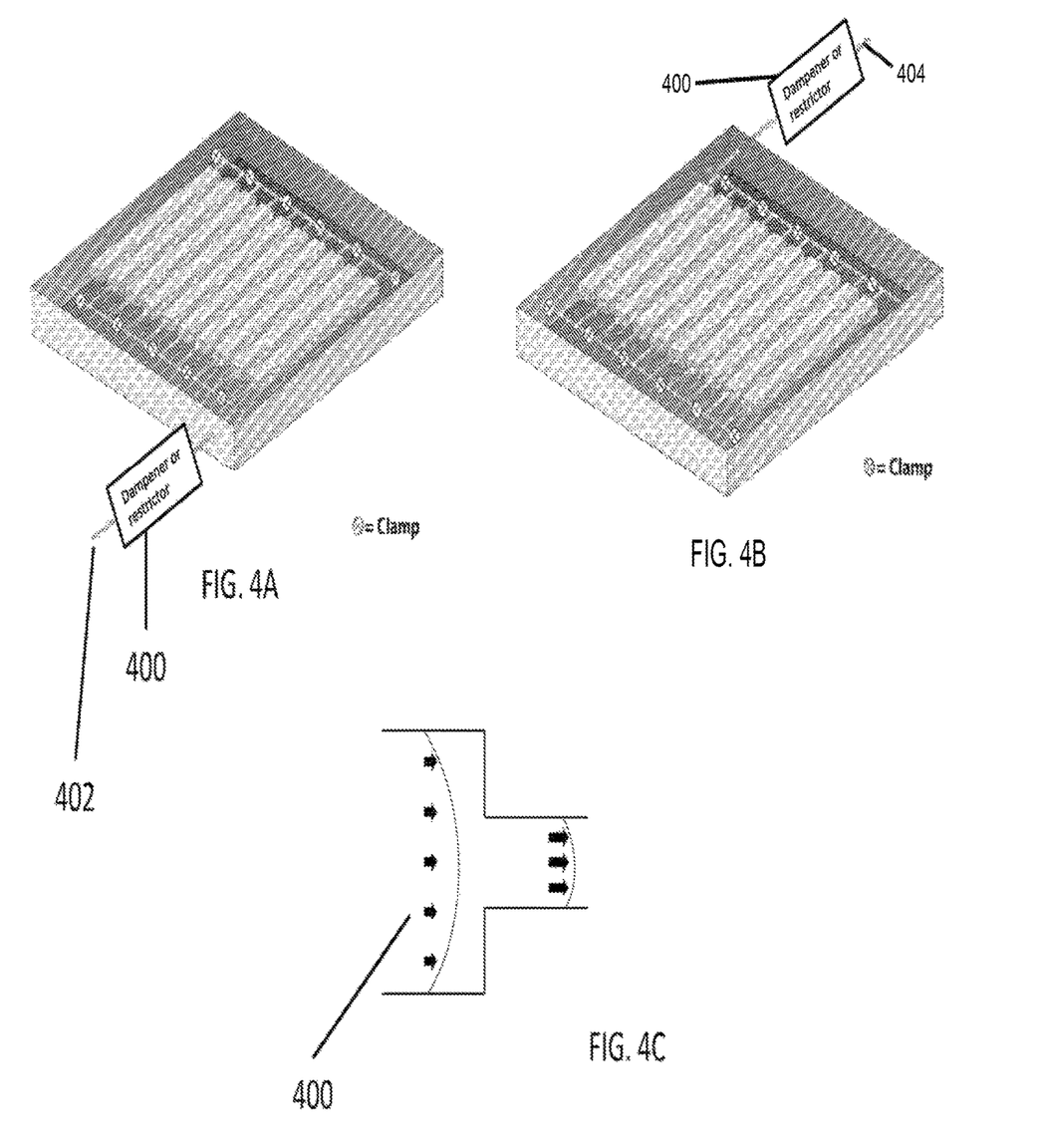
FIGS. 4A-B shows a fluid system for a plurality of bioreactors which includes a dampener component, according to some embodiments of the disclosure.
FIG. 4C shows a cross-sectional view of a flow restrictor and functionality corresponding thereto, according to some embodiments of the disclosure.

In some embodiments, pressure waves along a fluid flow path (in a fluid communication tube) from a pump (or other device/system) can cause variability in the total fluid pressure available at particular locations within the system; in particular, variability in pressure of the intraluminal fluids of the mandrel tubes. A dampener can be provided and arranged on a supply or return line (for example) of a fluid communication tube—e.g., containing the intra-luminal fluid flow, that is configured to substantially smooth the pressure variabilities. FIGS. 4A-B show example illustrations of the use and positioning of such dampeners 400 (as well as locations of clamps/valves—such terms used interchangeably and in some embodiments, perform the same functionality), and flow restrictors—see below—for example) to regulate variabilities in pressure waves within mandrel tubes of bioreactors within drawers, according to some embodiments of the present disclosure. In some embodiments, as discussed above, serial flow of fluids (such as the intra-luminal fluids, for example) allows each bioreactor to experience at least substantially similar fluid conditions, such as consistent nutrients, metabolites and/or dissolved gas profiles, etc., as a result of, amongst other reasons, at least comparable fluid flow rate in each of the bioreactors (e.g., compared to parallel fluid flows where multiple pumps can be used, leading to a possibility different flow rates between individual bioreactors). To maintain the at least substantially similar fluid conditions amongst bioreactors, in some embodiments, pulse dampeners can be located at intra-luminal fluid inlets 402 or outlets 404 (or both, depending upon the embodiments) of each drawer such that dampeners can push out against the inlet flow, for example (e.g., when a dampener is arranged with an inlet), and smooth out the flow.

In some embodiments, a flow resistor may be provided on a fluid supply/return line that is configured to maintain a baseline fluidic/hydrodynamic pressure along the paths of a fluid flow (e.g., the intra-luminal fluid flow from the reservoir through exiting the bioreactors). FIG. 4C is a cross-sectional illustration of the functionality of such a flow restrictor according to some embodiments (illustrating changes in flow and corresponding pressure differences). Such a flow resistor may be positioned along the tube or path leading from intra-luminal outlets of a drawer or bioreactors (for example) to an intra-luminal fluid waste disposal area (which can be the intra-luminal fluid reservoir itself, for example).

Figure 5:
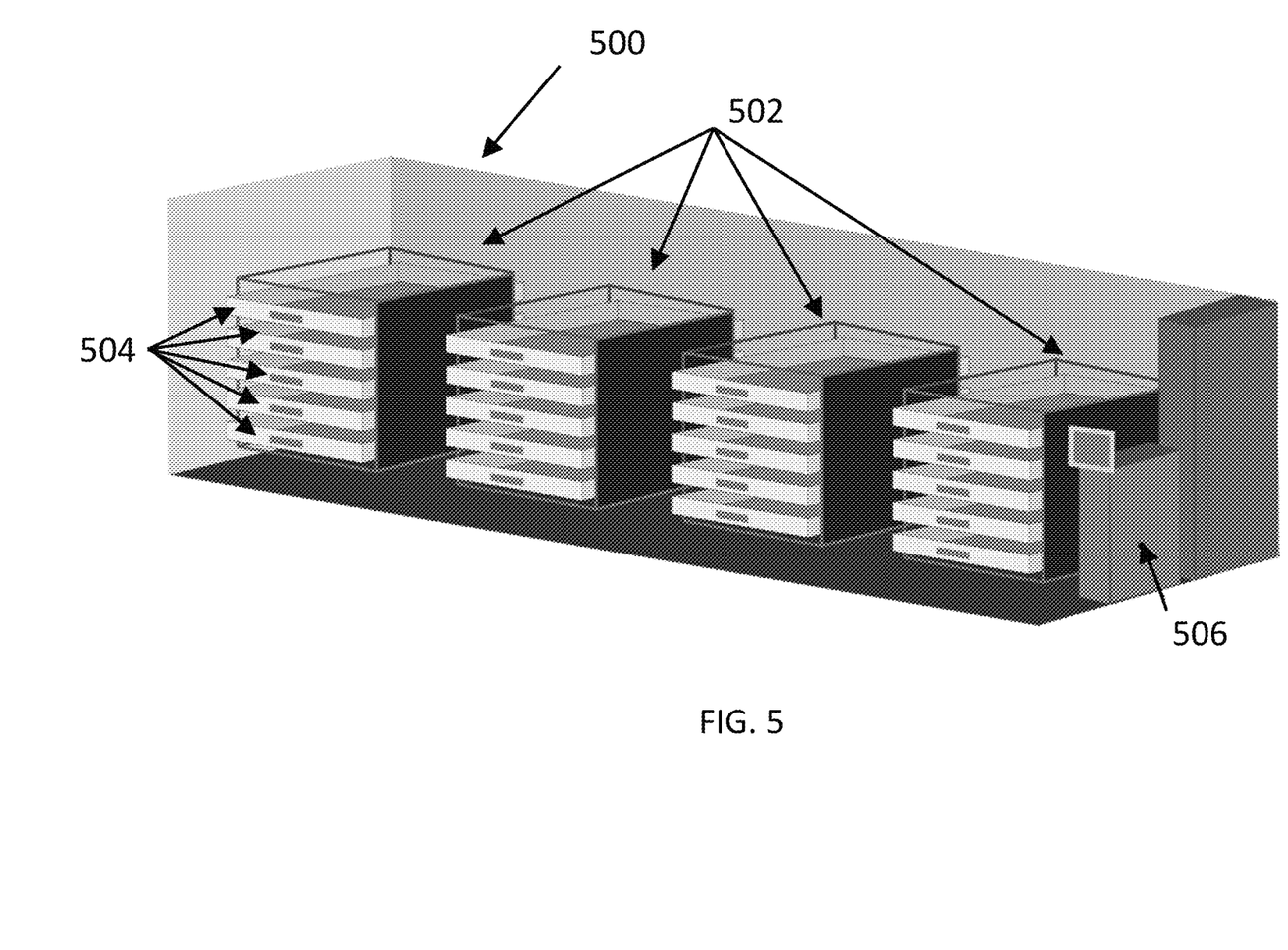
FIG. 5 shows a perspective view of an embodiment of a tissue cultivating system, according to some embodiments of the disclosure.

FIG. 5 shows an example embodiment of a multi-tiered platform 500, which may share one or more common reservoirs, according to some embodiments. As discussed above, in some embodiments, a plurality of drawers 504 can be included within each incubator shell 502, and the drawers can be coupled to a common set of reservoirs (e.g., biomedia reservoir, intra-luminal fluid reservoir, etc.) that provide biomedia, fluids, gases, etc. from a common source. In some embodiments, one, a plurality, or all of the drawers can also share a common MMM 506. Thus, in some embodiments, a plurality of drawers can be arranged in parallel to form a multi-tiered platform that is configured to allow for a simultaneous or near simultaneous production of large quantities of tissue (e.g., HAVs) while maintaining a reduced manufacturing footprint.

In some embodiments, the multi-tiered platform allows for consistent and reliable production of HAVs (or other tissues) as each bioreactor is likely to be exposed to at least substantially similar environmental and/or fluid conditions including but not limited to temperature, amount and type of dissolved gases, nutrients, fluid flow rates, and/or the like. Further, the parallel arrangement of the drawers containing bioreactors facilitates the sequential addition of biomedia, fluids, gases, etc., to all the incubators/drawers/bioreactors in parallel, if desired. Thus, and as noted earlier, the flow path for biomedia, fluids, gases, etc., circulating through the multi-tiered platform can be configured to be in serial, in parallel, or a hybrid of the two, allowing for enhanced control in how the HAVs are produced. For example, the flow of biomedia, fluids, gases, etc., in some or all drawers in the multi-tiered platform may be configured to be in parallel, for when the primary concern is the reduction or prevention of cross contamination of bioreactors during a de-cellularization step (for example) of the HAV production process (or other tissue cultivating process). In some embodiments, the multi-tiered platform allows for the change of tunable amount of cell culture media from the multi-tiered platform system at predetermined intervals.

Control of various embodiments of tissue cultivating systems disclosed herein, as well as one or more components and/or sub-systems thereof (and the making of HAVs for example) can be accomplished via hardware, software or a combination thereof. When implemented in software, the software code can be executed on any suitable processor or collection of processors, whether provided in a single computer or distributed among multiple computers.

In some embodiments, the combination of parallel and serial flow paths allows for biomedia, intra-luminal, and de-cellularization flows/fluids to be distributed in a manner that is advantageous for any one or more of the following reasons:
- ensures all of the bioreactors within the drawers are subjected to approximately identical conditions during the tissue growth and de-cellularization processes;
- reduces the number of bioreactor manipulations (e.g., aseptic connections/disconnections), and thus, decreases risks of contamination; and
- minimizes the number of pumps and/or valves required to reduce failure modes Typically, such systems are controlled by one or more computer programmable processors (either ASIC or via software) having one or more applications running thereon which operate one or more (and preferably all) of the pumps, motors, sensors, valves, clamps of the tissue cultivating systems disclosed herein. To this end, and as noted, one or more sensors can be provided to collect information (e.g., sense a condition) for any component and sub-system of the disclosed tissue cultivating systems which allow the controller to perform the cultivating process as so desired.

Accordingly, the controller/computer may be embodied in any of a number of forms, such as a rack-mounted computer, a desktop computer, a laptop computer, or a tablet computer (i.e., processor), server, and the like. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface which can be used to at least one of program, operate, and monitor the embodiments disclosed herein. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such controllers/computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety.

As noted elsewhere, the disclosed inventive embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to binding event determinative systems, devices and methods. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore, represent patentable subject matter and are distinguishable therefrom (i.e. claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for cultivating hollow, tubular tissues, comprising
a plurality of bioreactors arranged within at least one drawer, each bioreactor comprising a luminal space and an extra-luminal space, the luminal space comprising a tubular tissue circumferentially disposed on an outer surface of a hollow mandrel tube having a lumen, the hollow mandrel tube extending from a first end of the bioreactor to a second end of the bioreactor; and
a fluid management system comprising
at least one fluid reservoir, and
one or more fluid communication tubes configured to deliver, for each bioreactor within the at least one drawer, fluid from the at least one fluid reservoir
to the lumen of the hollow mandrel tube via a first inlet at the first end of the bioreactor, the first inlet in fluid communication with the lumen, and
to the extra-luminal space via a second inlet at the first end of the bioreactor, the second inlet in fluid communication with the extra-luminal space.

2. The system of claim 1, wherein
the at least one fluid reservoir comprises a biomedia fluid reservoir configured to contain biomedia fluid having one or more of nutrients and gases dissolved therein, and
the system further comprises:
an environmental control system configured to maintain the plurality of bioreactors at one or more of a predetermined temperature, humidity, and pressure, and
a controller for controlling at least one of operation of the system and one or more fluid flows of the fluid management system.

3. The system of claim 1, wherein the at least one drawer comprises a plurality of drawers.

4. The system of claim 2, wherein the at least one fluid reservoir further comprises an intra-luminal fluid reservoir configured to contain intra-luminal fluid having at least one of support, nutrients, and dissolved gases to cultivate tissue.

5. The system of claim 4, wherein the fluid management system further includes one or more gas dissolving means for dissolving one or more gases in at least one of the biomedia fluid, the biomedia fluid reservoir, the intra-luminal fluid, and the intra-luminal fluid reservoir.

6. The system of claim 5, wherein the one or more gas dissolving means comprises a sparger, and/or an inline gas media exchanger.

7. The system of claim 4, wherein
the system further comprises means to adjust heights between two or more of the biomedia reservoir, the intra-luminal reservoir, and the at least one drawer.

8. The system of claim 1, wherein:
each bioreactor further comprises one or more of:
a first outlet at the second end of the bioreactor, the first outlet in fluid communication with the first inlet via the lumen, a second outlet at the second end of the bioreactor, the second outlet in fluid communication with the second inlet via the extra-luminal space, and
a cell injection port, and
the fluid management system further comprises:
at least one of at least one tube organizer configured to at least one of arrange and direct the one or more fluid communication tubes among the bioreactors.

9. The system of claim 1, wherein the fluid management system further comprises at least one dampener arranged on at least one of the one or more fluid communication tubes, the at least one dampener being configured to smooth out variability in pressure in at least one of the fluid flow to and fluid flow from the plurality of bioreactors.

10. The system of claim 1, wherein the fluid management system further comprises at least one dampener arranged on at least one of the one or more fluid communication tubes, the at least one of the one or more fluid communication tubes being a tube in fluid communication with the first inlet at the first end of each bioreactor.

11. The system of claim 1, wherein the fluid management system includes at least one flow restrictor configured to restrict at least one of fluid flow to and fluid flow from the plurality of bioreactors.

12. The system of claim 11, wherein the at least one flow restrictor is arranged on at least one of the one or more fluid communication tubes, the at least one of the one or more fluid communication tubes being a tube in fluid communication with a first outlet at the second end of each bioreactor.

13. The system of claim 11, wherein the at least one flow restrictor is configured to control at least one of pressure and flow rate.

14. The system of claim 11, wherein the at least one restrictor is configurable to provide different flow restriction functionality based on a change of at least one of internal diameter, length, and material thereof.

15. The system of claim 11, wherein the at least one flow restrictor is arranged on a return line for returning an intra-luminal fluid from the plurality of bioreactors to an intra-luminal fluid reservoir.

16. The system of claim 1, wherein the fluid management system includes at least one waste port configured to direct at least one of waste biomedia fluid and waste intra-luminal fluid out of the system.

17. The system of claim 4, wherein the fluid management system further comprises:
at least one intra-luminal fluid pump,
at least one biomedia fluid pump, and
a plurality of valves arranged among the one or more fluid communication tubes.

18. The system of claim 17, wherein, during a fill operation, at least one of the at least one intra-luminal pump, the at least one biomedia pump, and the plurality of valves are configured to simultaneously fill each bioreactor with biomedia fluid from the biomedia fluid reservoir and intra-luminal fluid from the intra-luminal fluid reservoir.

19. The system of claim 17, wherein, during a processing operation, the at least one intra-luminal pump, the at least one biomedia pump, and the plurality of valves are configured to circulate biomedia fluid from the biomedia fluid reservoir serially through each of the plurality of bioreactors.

20. The system of claim 17, wherein the fluid management system is configured to, during a processing operation, circulate intra-luminal fluid serially through each lumen of each hollow mandrel tube of each bioreactor.

21. The system of claim 17, wherein the fluid management system is configured to, during a processing operation, flow intra-luminal fluid through each bioreactor in a direction opposite a direction of flow of biomedia fluid within each bioreactor.

22. The system of claim 17, wherein, during a drain operation, the at least one intra-luminal pump, the at least one biomedia pump, and the plurality of valves are configured to simultaneously drain each bioreactor of biomedia fluid and intra-luminal fluid.

23. The system of claim 17, wherein, during a drain operation, the fluid management system is configured to drain each bioreactor within a duration suitable for cell culture.

24. The system of claim 17, wherein the fluid management system is configured to, during a processing operation, flow intra-luminal fluid through each bioreactor in a same direction as a direction of flow of biomedia fluid within each bioreactor.

25. The system of claim 1, wherein a pressure of an intra-luminal fluid provided to the lumen of the hollow mandrel tube of the luminal space and a pressure of a biomedia fluid provided to the extra-luminal space establish a pressure differential across the tubular tissue within each bioreactor.

26. The system of claim 25, wherein the pressure differential across the tubular tissue is adjustable to provide a predetermined range of distension to the tubular tissue.

27. The system of claim 26, wherein the predetermined range of distension comprises negative distension and positive distension.

28. A system for cultivating hollow, tubular tissues, comprising
a plurality of bioreactors arranged within at least one drawer, each bioreactor comprising a luminal space and an extra-luminal space, the luminal space comprising a hollow mandrel tube having a lumen, the hollow mandrel tube extending from a first end of the bioreactor to a second end of the bioreactor; and
a fluid management system comprising
at least one fluid reservoir, and
one or more fluid communication tubes configured to deliver, for each bioreactor within the at least one drawer, fluid from the at least one fluid reservoir
to the lumen of the hollow mandrel tube via a first inlet at the first end of the bioreactor, the first inlet in fluid communication with the lumen, and
to the extra-luminal space via a second inlet at the first end of the bioreactor, the second inlet in fluid communication with the extra-luminal space.

* * * * *